United States Patent [19]

DeGeeter et al.

[11] 4,393,065
[45] Jul. 12, 1983

[54] ANIMAL FEED AND PROCESS

[75] Inventors: Melvin J. DeGeeter; John M. McCall, both of Kalamazoo; Dirk L. Teagarden, Portage, all of Mich.

[73] Assignee: The Upjohn Company, Kalamazoo, Mich.

[21] Appl. No.: 249,762

[22] Filed: Apr. 14, 1981

Related U.S. Application Data

[63] Continuation-in-part of Ser. No. 161,943, Jun. 23, 1980, Pat. No. 4,316,901, and a continuation-in-part of Ser. No. 161,944, Jun. 23, 1980, Pat. No. 4,307,093, and a continuation-in-part of Ser. No. 161,945, Jun. 23, 1980, Pat. No. 4,282,228, and a continuation-in-part of Ser. No. 161,946, Jun. 23, 1980, Pat. No. 4,315,930, and a continuation-in-part of Ser. No. 161,976, Jun. 23, 1980, Pat. No. 4,308,271.

[51] Int. Cl.$^3$ .................. A61K 31/505; A61K 27/00; A61K 31/54; A61K 31/53
[52] U.S. Cl. .................................. 424/251; 424/249; 424/248.53; 424/248.54; 424/248.55; 424/246; 424/248.56
[58] Field of Search ........... 424/251, 249, 246, 248.53, 424/248.56, 248.55, 248.54

[56] References Cited

U.S. PATENT DOCUMENTS 3,461,461  8/1969  Anthony et al. ................. 260/256.4

Primary Examiner—Frederick E. Waddell
Attorney, Agent, or Firm—John J. Killinger

[57] ABSTRACT

A process for increasing productivity in healthy animals comprising the administration of a compound of the formula

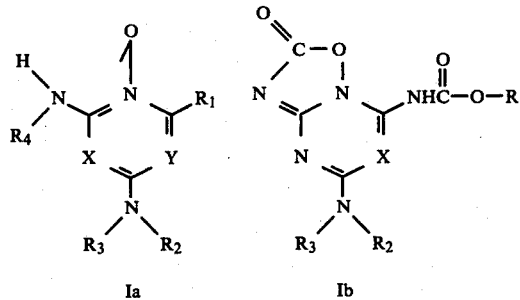

Ia                    Ib in association with the animal feed water or salt rations. Compositions comprising a compound of the above formula for daily administration or long acting forms are disclosed.

2 Claims, No Drawings

ANIMAL FEED AND PROCESS

CROSS REFERENCE TO RELATED APPLICATION

This application is a continuation-in-part of application Ser. Nos. 161,943, 161,944, 161,945, 161,946, and 161,976, all filed June 23, 1980 now U.S. Pat. Nos. 4,316,901; 4,307,093; 4,282,228; 4,315,930, and 4,308,271.

DESCRIPTION

BRIEF SUMMARY OF THE INVENTION

Broadly the present invention encompasses dosage form or a nutritionally adequate animal feed having dispersed therein a compound of the Formula Ia and Ib in sufficient concentration to provide increasing productivity and feed efficiencies in healthy meat-producing, milk-producing or egg-laying animals. The invention also includes the process of administering the compositions to healthy meat-producing, milk-producing, egg-laying or wool-producing animals.

BACKGROUND OF THE INVENTION

It has been found in recent years that meat-producing animals will gain more weight and gain it faster when various classes of compounds such as vitamins, minerals, estrogens, antibiotics, and tranquilizers are added to the diet. Although the presently available compounds are useful, new materials are still being sought that would produce weight gains more rapidly, to a greater extent, more efficiently with respect to feed intake at a lower cost and without undesirable side effects.

DETAILED DESCRIPTION OF THE INVENTION

It is now possible by use of the present invention to obtain unexpected results in the feeding of meat-producing, milk-producing, or egg-laying animals; that is to say, an increased rate of weight gain, an increased amount of weight gain, an increase in milk production enhanced wool production, or increased rate of egg laying, as well as increased feed efficiency, can be obtained by the addition of minute quantities of a compound of the Formula Ia or Ib to the animals usual nutrient feed drinking water or salt block or by administering short or long-acting dosage forms.

The active compounds are represented by the structure Ia or Ib:

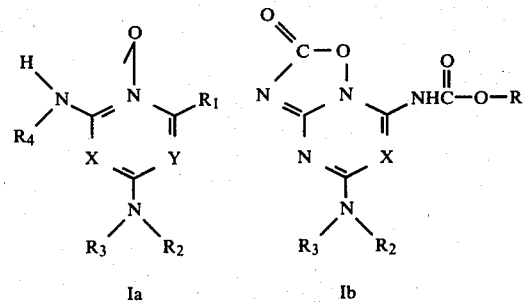

wherein
X is N or CH;
Y is N or $CR_5$;
R is alkyl of from 1 to 8 carbon atoms, inclusive, including isomeric forms thereof;
$R_1$ is R or

$R_2$ and $R_3$ are the same or different and are hydrogen, provided that $R_2$ and $R_3$ are not both hydrogen, R, cycloalkyl of from 3 to 8 carbon atoms, inclusive, alkyl substituted cycloalkyl of the formula

alkenyl of from 2 to 8 carbon atoms, inclusive, including isomeric forms thereof, aralkyl wherein
Ar is phenyl or substituted phenyl wherein 1 or 2 hydrogens are replaced with chlorine, fluorine, bromine, iodine, R, —OR, or $CF_3$, and the substituents can be the same or different, and alkyl is from 1 to 4 carbon atoms, inclusive, including isomeric forms thereof, and $R_2$ and $R_3$ taken together with —N< is a heterocyclic moiety of from 3 to 8, inclusive, ring atoms and 1 or 2 hetero atoms selected from the group consisting of nitrogen, oxygen or sulfur or a substituted heterocyclic moiety wherein 0, 1, 2, or 3 of the carbon atoms of the heterocycle are substituted with R;
$R_4$ is hydrogen,

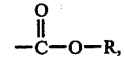

alkenyl of from 2 to 8 carbon atoms, inclusive, including isomeric forms thereof, cycloalkyl of from 3 to 7 carbon atoms, inclusive, or lower acyl wherein acyl is up to and including 5 carbon atoms;
$R_5$ is hydrogen, R, bromo or chloro;
$R_6$ is hydrogen,

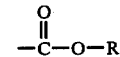

or lower acyl;
$R_7$ is hydrogen or alkyl of from 1 to 5 carbon atoms, inclusive, including isomeric forms thereof;
N is an integer of from 2 to 7, inclusive.

The compounds of the Formula Ia exist in tautomeric forms. It is to be understood that the compounds of this invention are likely to be mixtures of tautomeric forms, the compositions of which are dependent on such factors as the nature of the substituent groups and the environment. In some instances, one form or another may predominate.

Diazine compounds of the Formulas Ia can be prepared by methods disclosed in U.S. Pat. Nos. 3,910,928 (Oct. 7, 1975), 4,032,559 (June 28, 1977).

Pyridine compounds of the Formula Ia can be prepared by methods disclosed in U.S. Pat. No. 4,021,562.

Triazine compounds of the Formula Ia can be prepared by methods disclosed in U.S. Pat. Nos. 3,475,430, 3,270,014, 3,270,018, and 3,270,015.

Triazine compounds of the Formula Ib can be prepared by methods disclosed in Belgium Pat. No. 863,608, issued Mar. 18, 1978, and U.S. Pat. No.

4,150,131 substituting a triazine compound for the diazene of the patent.

Diazine compounds of the Formula Ib can be prepared by methods disclosed in Belgium Pat. No. 863,608, issued Mar. 18, 1978, and U.S. Pat. Nos. 4,175,190 and 4,150,131.

The compounds of Formulas Ia and Ib are amines, and exist in the non-protonated or free base form, or in the protonated or acid addition salt form, depending on the pH of the environment. They form stable protonates, i.e., mono- or diacid addition salts, on treatment with suitable acids, for example, hydrochloric, hydrobromic, sulfuric, phosphoric, nitric, acetic, benzoic, salicylic, glycolic, succinic, nicotinic, tartaric, maleic, malic, pamoic, methanesulfonic, cyclohexanesulfamic, picric, and lactic acids, and the like.

Examples of alkyl are methyl, ethyl, propyl, butyl, pentyl, hexyl, heptyl, octyl, and isomeric forms thereof. Examples of alkenyl are allyl, 1-methylallyl, 2-methylallyl (methallyl), 2-butenyl (crotyl), 3-butenyl, 1,2-dimethylallyl, 1,1-dimethylallyl, 2-ethylallyl, 1-methyl-2-butenyl, 2-methyl-2-butenyl, 3-methyl-2-butenyl, 3-pentenyl, 2,3-dimethyl-2-butenyl, 1,1,2-trimethylallyl, 1,3-dimethyl-2-butenyl, 1-ethyl-2-butenyl, 4-methyl-2-pentenyl, 2-ethyl-2-pentenyl, 4,4-dimethyl-2-pentenyl, 2-heptenyl, 2-octenyl, 5-octenyl, 1,4-dimethyl-4-hexenyl, and the like. Examples of cycloalkyl are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 3-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl and the like. Examples of aralkyl are benzyl, phenethyl, 1-phenylethyl, 2-phenylpropyl, 4-phenylbutyl, 5-phenyl-2-methylpentyl, 1-napthylmethyl, 2-(1-naphthyl)ethyl, 2-(2-naphthyl)-ethyl and the like. Examples of acyl are acetyl, propionyl, butanoyl, pentanoyl and the like. Examples of alkoxycarbonyl are carbomethoxy, carboethoxy and the like. Examples of heterocyclic moieties of the present invention are piperidino, pyrrolidinyl, morpholino, 2,4,4-trimethylazetidinyl, 2,3,4-trimethylazetidinyl, 2-methylpyrrolidinyl, 3-butylpyrrolidinyl, 2-isohexylpyrrolidinyl, 2,3-dimethylpyrrolidinyl, 2,2-dimethylpyrrolidinyl, 2,5-diethylpyrrolidinyl, 3-tert-butylpyrrolidinyl, 2,3,5-trimethylpyrrolidinyl, 3,4-dioctylpyrrolidinyl, 2-methylpiperidino, 3-methylpiperidino, 4-methylpiperidino, 3-isopropylpiperidino, 4-tert-butylpiperidino, 2-methyl-5-ethylpiperidino, 3,5-dipentylpiperidino, 2,4,6-trimethylpiperidino, 2,6-dimethylpiperidino, 2,6-dimethyl-4-octylpiperidino, 2,3,5-triethylpiperidino, 2-ethylhexahydroazepinyl, 4-tert-butylhexahydroazepinyl, 3-heptylhexahydroazepinyl, 2,4-dimethylhexahydroazepinyl, 3,3-dimethylhexahydroazepinyl, 2,4,6-tripropylhexahydroazepinyl, 2-methylheptamethylenimino, 5-butylheptamethylenimino, 2,4-diisopropylheptamethylenimino, 3,3-diethylheptamethylenimino, 2,5,8-trimethylheptamethylenimino, 3-methyloctamethylenimino, 2,9-diethyloctamethylenimino, 4-isooctyloctamethylenimino, 2-ethylmorpholino, 2-methyl-5-ethylmorpholino, 3,3-dimethylmorpholino, 2,6-di-tert-butylmorpholino, 4-methylpiperazinyl, 4-isopropylpiperazinyl, 2-methylaziridinyl, 2-ethylaziridinyl, 2-butylaziridinyl, 2,3-dimethylaziridinyl, 2,2-dimethylaziridinyl, 2-methylazetidinyl, 3-methylazetidinyl, 2-octylazetidinyl, 2,2-dimethylazetidinyl, 3,3-diethylazetidinyl and the like.

Unless otherwise specified, all percentages are given on a weight-to-weight basis. The pound (lb) weights given are avoirdupois units.

Administration of the compositions of the present invention can commence for birds shortly after hatching and in the case of mammals, during the creep-feeding period of suckling animals when they are starting on solid food and, of course, after weaning. Feeding of the compositions is continued throughout the growing period, lactation period, or egg-laying period. In addition to feeding the active ingredient in combination with the feed, the active compounds can alternatively be administered in combination with the animals drinking water or in combination with a pharmaceutical carrier by injection or implantation.

The total concentration of the compound of the Formula Ia or Ib in the feed composition is determined with regard to the species of animal, sex, age, weight, and average amount of feed consumed daily. Preferably the compound of the Formula I is employed in the finished feed that will supply the animal with a daily intake of from about 0.02 mg to about 200 mg per head, per day.

The following table illustrates the range of compound of Formula Ia or Ib in milligrams daily dose, per head, per day for representative animals.

| Animal | Range Daily Dose/Head, mg | Preferred Daily Dose, mg |
| --- | --- | --- |
| Swine (birth to 8 weeks) | 0.5–20.0 | 10.0 |
| Swine (40 to 200 lbs) | 1.0–140.0 | 10.0 |
| Chickens (growing 0–8 weeks) | 0.02–2.0 | 0.05 |
| Hens (laying) | 0.1–2.0 | 1.0 |
| Turkeys (growing 0–24 weeks) | 0.1–5.0 | 2.0 |
| Beef Cattle (fattening) | 0.5–50.0 | 10 |
| Calves (0–12 weeks) | 1.0–40.0 | 10 |
| Dairy Cattle (lactation) | 5.0–200.0 | 10 |
| Lambs (fattening) | 1.0–20.0 | 10 |

The foregoing dosages can generally be accomplished by providing from about 50 mg to about 20,000 mg of a compound of the Formula Ia or Ib per ton of finished feed.

Advantageously a compound of the Formula Ia or Ib is supplied in the form of a liquid or solid premix wherein the concentration is 100–2,000 times greater than the desired final concentration in the feed. For example, the compound of Formula Ia or Ib can be dissolved or suspended in a fluid vehicle such as corn oil, cottonseed oil, molasses, distillers solubles and the like to prepare a fluid premix. Alternatively, a solid premix can be prepared by mixing a compound of the Formula Ia or Ib with an edible solid diluent such as sucrose, lactose, starch, corn meal, flour, calcium carbonate, soybean meal and the like.

EXAMPLE 1

A diet for fattening lambs is prepared from the following types and amounts of ingredients:

| | |
|---|---|
| Ground ear corn | 82.35% |
| Alfalfa meal | 10.0% |
| Soybean oil meal 44% | 7.0% |
| Ground limestone | 0.3% |
| Salt | 0.3% |
| Trace mineral mixture[1] | 0.05% |

[1]Contains the following percent of minerals: Mn, 12; Co, 0.08; Fe, 5.0; Cu, 0.4; I, 0.24; Zn, 0.7.

The above feed to be mixed, pelleted and offered to fattening lambs free-choice in conjunction with hay.

To 999 parts of the preceding feed is added 1 part of a premix composition prepared by mixing 7 gm of 2,4-diamino-6-piperidinopyrimidine-3-oxide with sufficient corn meal to make one pound.

The feeding composition so prepared supplies 7.0 mg of 2,4-diamino-6-piperidinopyrimidine-3-oxide per pound or 15.4 parts per million.

The foregoing composition is usefully fed to lambs for increased rate of weight gain and improved utilization of feed.

EXAMPLE 2

A chicken feed for broilers is prepared from the following types and amounts of ingredients:

| | |
|---|---|
| Yellow corn meal | 67.35% |
| Soybean oil meal | 24.00% |
| Menhaden fish meal | 6.00% |
| Steamed bone meal | 1.00% |
| Ground limestone | 1.00% |
| Iodized salt | .34% |
| 25% Choline chloride | .13% |
| Vitamin $B_{12}$ supplement (6 mg/lb) | .10% |
| Manganese sulfate | .02% |
| Supplemental vitamin mix[1] | .06% |

[1]Consisting of 16.0 gm Vitamin A supplement (10 units/mg); 3.6 gm Vitamin $D_3$ supplement (15,000 units/gm); 7.1 gm riboflavin supplement (1 gm riboflavin per ounce); 500 mg niacin.

To 999 parts of the preceding feed is added 1 part of a premix composition prepared by mixing 0.38 gm of 2,4-diamino-6-piperidinopyrimidine-3-oxide with sufficient soybean mill feed to make 1 pound.

The feeding composition so prepared supplies 0.38 mg of 2,4-diamino-6-piperidinopyrimidine-3-oxide per pound, or about 0.83 parts per million.

The foregoing composition is usefully fed to chickens for increased rate of weight gain and improved utilization of feed. Similarly the composition can be fed to turkeys, ducks and geese.

EXAMPLE 3

A fattening feed for 800 pound yearling cattle is prepared from the following types and amounts of ingredients:

| | |
|---|---|
| Ground ear corn | 89.75% |
| Soybean oil meal, 44% | 9.0% |
| Ground limestone | 0.7% |
| Salt | 0.5% |
| Trace mineral mixture[1] | 0.05% |

[1]Contains the following percent of minerals: Mn, 12, Co, 0.08; Fe, 5.0; Cu, 0.4; I, 0.24; Zn, 0.7.

To 999 parts of the preceding feed is added 1 part of a premix composition prepared by mixing 0.5 gm of 2,4-diamino-6-piperidinopyrimidine-3-oxide with sufficient wheat flour to make 1 pound.

The feeding composition so prepared supplies 0.5 mg of 2,4-diamino-6-piperidinopyrimidine-3-oxide per pound, or about 1.10 parts per million.

Cattle are to receive the foregoing feed ad libitum together with 5 lbs. of hay, per head, per day and when so fed have an increased rate of weight gain and improved utilization of feed.

EXAMPLE 4

A swine diet for growing hogs of 40 to 100 pounds body weight is prepared from the following types and amounts of ingredients:

| | |
|---|---|
| Corn, ground | 78.15% |
| Soybean oil meal, 44% | 17.0% |
| Meat and bone scraps, 50% | 3.0% |
| Oyster shell flour | 0.4% |
| Bone meal | 0.5% |
| Salt | 0.5% |
| Trace mineral mixture | 0.05% |
| Zinc oxide | 0.01% |
| Vitamin A and D Supplement[2] | 0.25% |
| Vitamin Supplement[3] | 0.05% |
| Vitamin $B_{12}$ Supplement[4] | 0.09% |

[1]Contains the following % of minerals: Mn, 12; Co, 0.08; Fe, 5.0; Cu, 0.4; I, 0.24; Zn, 0.7.
[2]Contains 300 USP units $D_2$/Gm and 1500 IU of A/Gm
[3]Contains per lb: Riboflavin, 2000 mg; calcium pantothenate, 4000 mg; niacin, 9000 mg; and choline chloride 10,000 mg.
[4]Contains 6 mg Vitamin $B_{12}$ per lb.

To 999 parts of the preceding feed is added 1 part of a premix composition prepared by mixing 2 g of 2,4-diamino-6-piperidinopyrimidine-3-oxide with sufficient ground limestone to make one pound.

The feeding composition so prepared supplies 2 mg of 2,4-diamino-6-piperidinopyrimidine-3-oxide per pound or about 4.4 parts per million.

The foregoing composition is usefully fed to hogs for increased rate of weight gain and improved utilization of feed.

EXAMPLE 5

A regimen of 2,4-diamino-6-piperidinopyrimidine-3-oxide in water is prepared simply by adding the compound to the drinking water as specified below. The animals are allowed to ingest the water on an ad lib basis.

| | | mg/l |
|---|---|---|
| Swine | Birth to 8 weeks | 2.5 |
| Swine | 40–200 lb | 7.0 |
| Chickens | 0–8 weeks | 0.3 |
| Hens | | 5.0 |
| Turkeys | 0–24 weeks | 3.2 |
| Beef cattle | | 0.2 |
| Calves | 0–12 weeks | 1.0 |
| Dairy cattle | | 0.9 |
| Lambs | | 5.0 |

EXAMPLE 6

Following the procedure of the preceding Examples 1 to 5, inclusive, animal feeds are similarly prepared substituting equimolar amounts of:
2,4-diamino-6-pyrrolidinopyrimidine-3-oxide,
2,4-diamino-6-diethylaminopyrimidine-3-oxide,
2,4-diamino-6-(2-methylpiperidino)pyrimidine-3-oxide, 2-amino-4-methyl-6-pyrrolidinopyrimidine-3-oxide,
2-amino-4-methyl-6-piperidinopyrimidine-3-oxide,
2,4-diamino-6-dialkylaminopyrimidine-3-oxide,
2,4-diamino-6-piperidino-S-triazine-3-oxide,
2,4-diamino-6-pyrrolidino-S-triazine-3-oxide,
2-amino-4-methyl-6-pyrrolidino-S-triazine-3-oxide,
2,4-diamino-6-diethylamino-S-triazine-3-oxide,
2,4-diamino-6-(N,N-dialkylamino)-S-triazine-3-oxide,
2,6-diamino-4-pyrrolidinopyridine-1-oxide,
2,6-diamino-4-diethylaminopyridine-1-oxide,
2,6-diamino-4-(2-methylpiperidino)pyridine-1-oxide,
2-amino-6-methyl-4-pyrrolidinopyridine-1-oxide,
2-amino-6-methyl-4-piperidinopyrimidine-1-oxide,
2,6-diamino-4-dialkylaminopyrimidine-1-oxide,
2,6-diamino-3-piperidinopyrimidine-1-oxide,
ethyl[2-oxo-5-(1-piperidinyl)-2H-[1,2,4]oxadiazolo-[2,3-a]pyrimidin-7-yl]carbamate,
ethyl[5-[3,6-dihydro-1(2H)-pyridyl]-2-oxo-2H-[1,2,4]-oxadiazolo-[2,3-a]pyrimidin-7-yl]carbamate,
butyl[5-[3,6-dihydro-1(2H)-pyridyl]-2-oxo-2H-[1,2,4]oxadiazolo-[2,3-a]-pyrimidin-7-yl]carbamate,
ethyl[5-dialkylamino-2-oxo-2H-[1,2,4]-oxadiazolo[2,3-a]-pyrimidin-7-yl]carbamate,
ethyl[5-diethylamino-2-oxo-2H-[1,2,4]oxadiazolo[2,3-a][1,3,5]-triazin-7-yl[carbamate;
ethyl[5-diallylamino-2-oxo-2H-[1,2,4]oxadiazolo[2,3-a][1,3,5]-triazin-7-yl[carbamate,
ethyl[5-[3,6-dihydro-1(2H)-pyridyl]2-ox-2H-[1,2,4]oxadiazolo-[2,3-a][1,3,5]triazin-7-yl]carbamate, and
ethyl[2-oxo-5-(1-piperidinyl)-2H-[1,2,4]oxadiazolo[2,3-a]-[1,3,5-]triazin-7-yl]carbamate.
for the 2,4-diamino-6-piperidinopyrimidine-3-oxide of the example.

An added advantage was observed in the feeding of sheep. The sheep produced an increased amount of wool. This increase in wool production was attributable to the increase in body size (and weight).

In addition to the daily administration of a compound of the formulas Ia and Ib, in association with the animal feed or drinking water, daily administration can be accomplished by incorporation of the active compound in a salt block in an amount calculated to provide the active compound based upon the daily salt intake of the animal.

In animals that are on open range or for whom daily administration is inconvenient a long active carrier can be prepared for the active compound. Long acting forms can be implants which are placed under the animals skin, injectable fluids or in the case of ruminants, an oral bolus.

Implants are prepared for 30 or 90 day administration incorporating 30 to 90 times the daily dose in an inert carrier material. The carrier material can be non-degradable by the animals body, e.g. silicone rubber, polyethylene or hydrophilic polymers such as hydron, or degradable polymers such as polyactic acid, polyacetic acid/polyglycolic acid copolymer, poly(orthoester), poly (E-caprolactone) or polyglutamic acid. Implants are conveniently implanted in the neck of the chicken, the dewlap of the calf, ear of the pig, or flank of goats and lambs.

Long acting (90 day) injectable can be prepared incorporated 90 times the daily dose of a compound of the Formula Ia or Ip preferably a water insoluble derivatives such as the acyl diacyl or carbamate form in combination with a sterile injectable fluid carrier such as water, polyethylene glycol 400, propylene glycol or water.

Long acting orally administered forms, e.g., a bolus can be prepared for ruminant animals. The bolus can be prepared by the same materials as the implant but is made in a much larger size and advantageously has added excipients to increase the specific gravity of the devise. The bolus when administered remains in the reticulum or rumen of the animal and releases the drug over the desired period of time. Excipients to increase specific gravity can be for example, iron pellets, calcium sulfate dihydrate portland cement or plaster of paris.

EXAMPLE 7

Salt Block

Salts blocks are prepared for cattle containing for 0.001 to 0.04 percent w/w with 0.004 percent w/w being preferred. The cattle are allowed free access to the salt block for self administration ad libitum.

Salt blocks for sheep are prepared in a concentration of from 0.0024 to 0.048 percent w/w with 0.024 being preferred.

EXAMPLE 8

Long Acting Injectable Fluid

A long acting injectable fluid is prepared by the following types and amount of ingredients:

| | | |
|---|---|---|
| 2-Amino-4-valeramido-6-piperidinopyrimidine-3-oxide | 1.8 | gram |
| Benzyl alcohol | 0.1 | gram |
| Carboxymethylcellulose | 0.1 | gram |
| NaCl | 0.09 | gram |
| Tween 80 | 0.1 | gram |
| Propylene glycol q.s. | 10. | ml |

The ingredients are mixed under aseptic conditions.
The composition when injected, 5 ml, into calves, beef or dairy cattle or lambs provides 10 mg of drug 1 day for 90 days.

EXAMPLE 9

Inplant

A silicone rubber implant is prepared for the following types and amounts of ingredients.

| | |
|---|---|
| 2,4-Diamino-6-piperidinopyrimidine-3-oxide | 0.72 gram |
| Stannous octoate | 0.26 gram |
| Dimethylpolysiloxane (Dow Corning Silastic 382) | 99. gram |

The ingredients are mixed well and placed in a cyclindrical mold and cured.
The silastic device is implanted on the dewlap of a calf or flank of a sheep or goat for 90 days of release.
For pigs the active compound is increased to 3.6 gram and the device placed in the tissue under the ear.

EXAMPLE 10

Bolus for Ruminants (A) A thirty day bolus is prepared for the following types and amount of ingredients.

2,4-Diamino-6-piperidinopyrimidine-

-continued

| | |
|---|---|
| 3-oxide | .3 gram |
| Mg stearate | .5 gram |
| CaSO₄ dihydrate q.s. | 100.0 gram |

The bolus is prepared by mixing the ingredients together and compression. The bolus provides 30 days treatment for goats, sheep or cattle.

(B) 90 Day bolus

| | |
|---|---|
| 2,4-Diamino-6-piperidinopyrimidine-3-oxide | .9 gram |
| Mg stearate | .5 gram |
| CaSO₄ dihydrate q.s. | 100.0 gram |

The bolus is prepared by mixing the ingredients and compression. The bolus provides 90 days treatment for goats, sheep or cattle.

We claim:

1. A process for obtaining increased meat, milk, egg or wool production in healthy animals comprising the administration to a healthy animal a long acting composition containing an effective amount of a compound of the formula

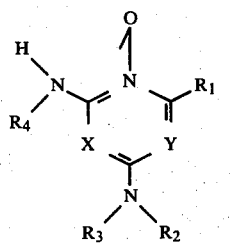

wherein

X is N;

Y is CR₅;

R is alkyl of from 1 to 8 carbon atoms, inclusive, including isomeric forms thereof;

R₁ is R or

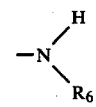

R₂ and R₃ are the same or different and are hydrogen, provided that R₂ and R₃ are not both hydrogen, R, cycloalkyl of from 3 to 8 carbon atoms, inclusive, alkyl substituted cycloalkyl of the formula

alkenyl of from 2 to 8 carbon atoms, inclusive, including isomeric forms thereof, aralkyl wherein Ar is phenyl or substituted phenyl wherein 1 or 2 hydrogens are replaced with chlorine, fluorine, bromine, iodine, R, —OR, or CF₃, and the substituents can be the same or different, and alkyl is from 1 to 4 carbon atoms, inclusive, including isomeric forms thereof; and P₂ and R₃ taken together with —N< is a heterocyclic moiety of from 3 to 8, inclusive, ring atoms and 1 or 2 hetero atoms selected from the group consisting of nitrogen, oxygen or sulfur or a substituted heterocyclic moiety wherein 0, 1, 2, or 3 of the carbon atoms of the heterocycle are substituted with R;

R₄ is hydrogen,

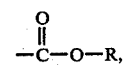

alkenyl of from 2 to 8 carbon atoms, inclusive, including isomeric forms thereof, cycloalkyl of from 3 to 7 carbon atoms, inclusive, or lower acyl wherein acyl is up to and including 5 carbon atoms;

R₅ is hydrogen, R, bromo or chloro;

R₆ is hydrogen,

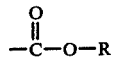

or lower acyl;

R₇ is hydrogen or alkyl of from 1 to 5 carbon atoms, inclusive, including isomeric forms thereof;

n is an integer of from 2 to 7, inclusive, said composition being in the form of an implant, bolus, or sterile injectable.

2. The process of claim 1 wherein the compound is 2,4-diamino-6-piperidinopyrimidine-3-oxide.

* * * * *